(12) United States Patent
Kani et al.

(10) Patent No.: US 8,712,013 B2
(45) Date of Patent: Apr. 29, 2014

(54) MOTION CONTROL SYSTEM AND X-RAY MEASUREMENT APPARATUS

(75) Inventors: Tetsuo Kani, Yokohama (JP); Tomoyasu Ueda, Hamura (JP); Kiyoshi Ogata, Mianto (JP); Kazuhiko Omote, Akiruno (JP); Kenji Wakasaya, Akishima (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 288 days.

(21) Appl. No.: 13/219,966

(22) Filed: Aug. 29, 2011

(65) Prior Publication Data
US 2012/0053733 A1    Mar. 1, 2012

(30) Foreign Application Priority Data
Aug. 30, 2010    (JP) ................ 2010-192560

(51) Int. Cl.
*G01N 23/20*    (2006.01)

(52) U.S. Cl.
USPC .......................................................... 378/81

(58) Field of Classification Search
USPC .................. 378/79, 81; 250/231.16; 235/436; 318/651
See application file for complete search history.

(56) References Cited

U.S. PATENT DOCUMENTS

| | | | |
|---|---|---|---|
| 6,084,234 A | 7/2000 | Stridsberg | |
| 7,143,518 B2 | 12/2006 | Watanabe et al. | |
| 2001/0013765 A1 | 8/2001 | Yamamoto et al. | |
| 2005/0168187 A1 | 8/2005 | Uchiyama et al. | |
| 2006/0250104 A1* | 11/2006 | Reichert et al. | 318/651 |
| 2011/0139873 A1 | 6/2011 | Sprenger | |

FOREIGN PATENT DOCUMENTS

| | | |
|---|---|---|
| JP | 2003-262518 A | 9/2003 |
| JP | 2006-098392 A | 4/2006 |
| WO | WO 95/16185 A1 | 6/1995 |
| WO | WO 2010/028963 A2 | 3/2010 |

OTHER PUBLICATIONS

Search Report dated Dec. 21, 2011, issued in the corresponding United Kingdom Patent Application No. GB1115012.5. (4 pages).

* cited by examiner

*Primary Examiner* — Courtney Thomas
(74) *Attorney, Agent, or Firm* — Buchanan Ingersoll & Rooney PC

(57) ABSTRACT

A motion control system comprising a servo motor for moving a rotary stage; a scale provided on the rotary stage or on an object that moves integrally with the rotary stage; a plurality of reading heads for detecting the scale and outputting a signal; a data processing part for calculating an average value of rotation angle data based on each of the output signals from the reading heads and outputting the average value as a signal; and a servo amplifier for controlling the motor based on the signal representing the average value of the rotation angle. The motion control system can cause the rotary stage to rotate to a desired rotation angle to a high degree of accuracy using the reading heads.

9 Claims, 14 Drawing Sheets

F I G. 1
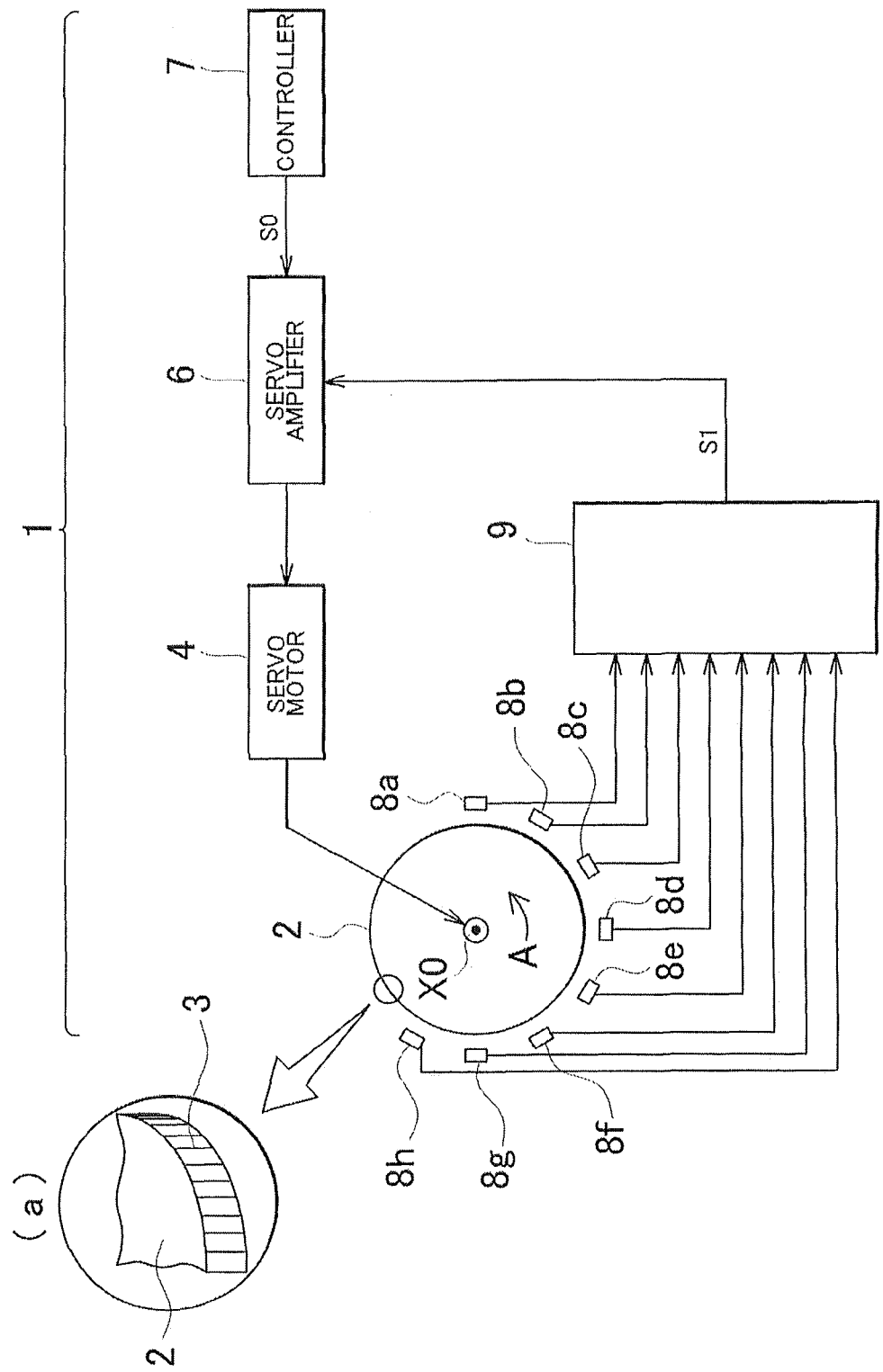

(INTERPOLATION)

(ANGLE COMPUTATION PROCESS 1)

(ANGLE COMPUTATION PROCESS 2)

( ANGLE COMPUTATION PROCESS 3 )

(ANGLE COMPUTATION PROCESS 4)

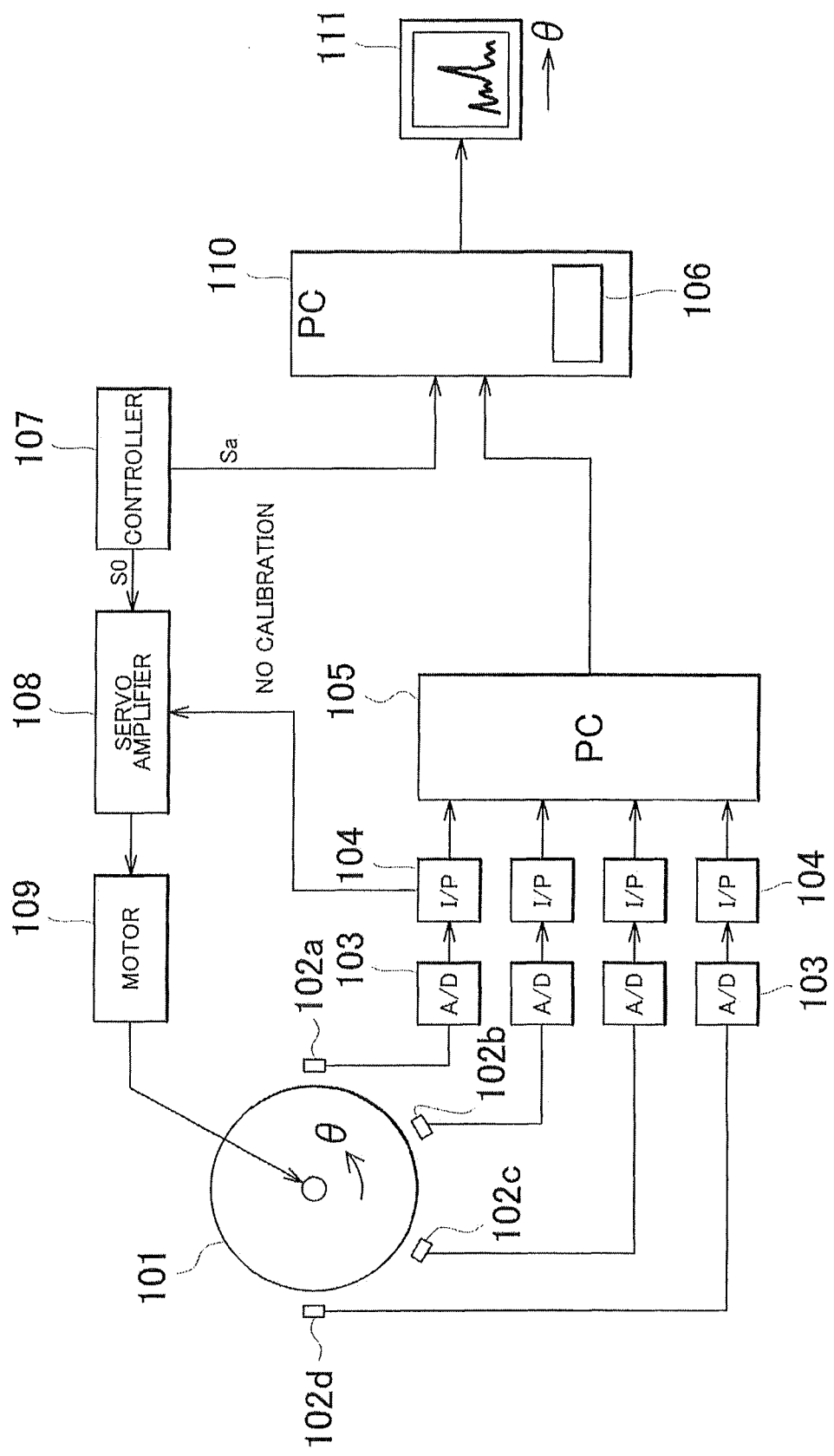

US 8,712,013 B2

MOTION CONTROL SYSTEM AND X-RAY MEASUREMENT APPARATUS

BACKGROUND OF THE INVENTION

1. Field of the Invention

The present invention relates to a motion control system for moving a moving body by a desired amount of movement, e.g., a motion control system such as a goniometer for causing a rotating body to rotate by a desired angle. The present invention also relates to an X-ray measurement apparatus comprising the motion control system of above description.

2. Description of the Related Art

Motion control systems for moving a moving body by a desired amount of movement are widely used in a variety of industrial sectors, such as machine tools, motor vehicles, robots, measurement instruments, and other fields. For example, in the field of measurement instruments, a goniometer, which functions as a motion control system, is sometimes used to cause a rotary stage to rotate in an instance in which the rotary stage, which functions as a moving body and which supports a specimen to be measured, is caused to rotate by a desired angle.

A goniometer of such description has, e.g., an electric motor, which functions as a power source for causing the rotary stage to rotate, and an angle detector for detecting the angle of rotation of the rotary stage. Conventionally known angle detectors of such description include that disclosed in Patent Citation 1. In this angle detector, one angle data detection head, which functions as a reference; and a plurality of nth degree error component detection heads are arranged around a rotating disc; respective output data from each of the nth degree error component detection heads is applied to a predetermined computation formula to obtain an nth degree error component; the nth degree error component is subtracted from output data from the reference head; whereby the output data is calibrated and highly accurate angle data having minimal error is obtained. Patent Citation 1 also discloses a technique in which a table, comprising the nth degree error components and angle values, is utilized according to need.

Patent Citation 1 does not mention methods for utilizing calibrated angle data that has been obtained as described above. One general method of utilizing calibrated angle data of such description is a processing system such as that shown in FIG. 14, in which a common personal computer is used. In this system, a plurality of detection heads 102a through 102d, including a reference detection head 102a, are arranged at appropriate angular intervals around an encoder disc 101 provided with a calibration (i.e., a scale).

The encoder disc 101 is integrally connected to a rotating body (not shown), the rotating body being driven by a servo motor 109, which is an electric motor. The encoder disc 101 rotates integrally with the rotating body. The angle of rotation of the servo motor 109 is controlled by a servo amplifier 108. The servo amplifier 108 controls the angle of rotation of the servo motor 109, based on an angle instruction signal S0 sent from a controller 107. The controller 107 transmits an angle signal Sa to a second personal computer 110.

An analog output signal from each of the detection heads 102a through 102d is converted into a digital signal by an analog-digital converter (ADC) 103, and is subjected to an n-fold increase in frequency by an interpolator 104 (i.e., n-fold interpolation). Data after interpolation is subjected to predetermined computation by a personal computer 105, data for calibration is obtained, and the data for calibration is transmitted to the second personal computer 110. The personal computer 110 creates a calibration table 106 based on the transmitted data.

The second personal computer 110 calibrates, using the calibration data stored in the angle calibration table 106, the angle signal Sa sent from the controller 107. The calibrated angle data is deemed to be the correct angle data. The correct angle data is reflected on, e.g., a screen of a display 111, which is an output instrument. The method for utilizing the angle calibration table 106 shown in FIG. 14 is an example, and a variety of other utilization methods can be envisaged.

In general, in an instance in which there are a plurality of angle data processing systems shown in FIG. 14, even if the mechanical and electrical constituent elements that form each of the systems are completely identical, characteristics of the assembled angle data processing systems will be inconsistent. Therefore, calibration data stored in the angle calibration table 106 is different between each of the angle data processing systems.

Also, mechanical and electrical characteristics of the angle data processing systems change over time. Therefore, as a rule, the content of the angle calibration table 106 must be modified over time. Also, in an instance in which, as an option, an auxiliary load is placed on the moving body (e.g., a rotary stage) onto which the encoder disc 101 is mounted, the moving body may deform as a result of unbalanced load, and the angle calibration table 106 must be re-created each time this occurs.

As described above, calibration data in the angle calibration table 106 must be created for each angle control system, and even data for a single control system must be modified over time. Management of the angle calibration table 106 is extremely troublesome.

A conventional angle detector, similar to the angle detector used in the angle data processing system shown in FIG. 14, is disclosed in Patent Citations 2 and 3. Patent Citation 3 is a U.S. patent specification based on Patent Citation 2. In these patent citations, there is disclosed an angle data processing system in which one second calibration-reading head, which represents a reference, and a plurality of first calibration-reading heads are arranged around a calibration plate, which corresponds to an encoder disc. In this processing system, a difference in measurement between the single second calibration-reading head and each of the first scale reading heads is obtained; an average of the differences is obtained; a calibration curve is obtained based on the average of the differences; the calibration curve is used to calibrate the output data of the second calibration-reading head, which is the reference; and the calibrated data used as the final angle data.

Patent Citations 2 and 3 do not mention methods for utilizing the calibrated angle data obtained as described above. In general, an angle data processing system such as that described further above and shown in FIG. 14, i.e., a system for performing a process in which the angle signal Sa from the controller 107 is calibrated using the angle calibration table 106 and outputted when required, can be envisaged.

[Patent Citation 1] JP-A 2003-262518 (pages 2 and 3, FIGS. 1 through 4)
[Patent Citation 2] JP-A 2006-098392 (pages 3 through 5, FIG. 1)
[Patent Citation 3] U.S. Pat. No. 7,143,518

SUMMARY OF THE INVENTION

As described above, according to a conventional detection technique, in an instance in which a plurality of detection heads are used to detect an amount of movement to a high degree of accuracy, a reference detection head is defined from among a plurality of detection heads; errors between the reference head and other heads are obtained; a calibration curve for the reference head is obtained based on the errors; and detection results measured by the reference head is calibrated using the calibration curve; whereby the correct amount of movement of a rotary stage is obtained.

However, according to this method, the procedure of processing the measured data is complex, and it is difficult to perform computation in a short time. It is therefore difficult to utilize feedback control. Accordingly, it is not possible, after measured data is detected by a plurality of detection heads, to control the rotation of the rotary stage in an immediate manner (i.e., in real-time) based on the data.

With the above-mentioned problems regarding conventional apparatuses in view, an object of the present invention is to provide a motion control system in which, when computationally obtaining a correct amount of movement using a plurality of detection heads, a processing procedure is simplified and processing time is shortened to allow feedback control, whereby a rotary stage or another moving body can be moved (e.g., caused to rotate) by a desired amount of movement (e.g., rotation angle) to a high degree of accuracy.

A motion control system according to the present invention is a motion control system for moving a moving body by a desired amount of movement, the motion control system comprising:

moving-body-driving means for moving the moving body;

a scale provided on the moving body or on an object that moves integrally with the moving body;

a plurality of scale-detecting means for detecting the scale and outputting a signal;

computation means for calculating an average value of the amount of movement based on each of the output signals from the scale-detecting means, and outputting the average value of the amount of movement as a signal; and control means for controlling the moving-body-driving means based on the signal representing the average value of the amount of movement.

In the present invention, information from the scale-detecting means is averaged, error is removed, information from which error has been removed as described above is transmitted to the control means, and feedback control is performed. In the configuration described above, the moving-body-driving means may be a servo motor, and in some instances, may be a stepping motor, DC motor, ultrasonic motor, linear motor, or similar means.

The moving body is, e.g., a rotating body, a linearly moving body, or another moving body. The amount of movement refers to a rotation angle in an instance of a rotating body, and to an amount of linear movement in an instance of a linearly moving body. An example of a rotating body is a rotary stage that rotates about its own center axis. An example of a linearly moving body is a moving body that uses a ball screw or another screw axis. An example of a linearly moving body is a rotor of a linear motor. In this instance, the linear motor functions as the moving-body-driving means. In the instance of a linearly moving body, the effect of mechanical error and similar error is simply detected using a plurality of detectors. Possible causes of errors include error in mounting the scale or machining error.

According to the present invention, the computation means calculates the average value of the amount of movement based on output signal from the plurality of scale-detecting means. Therefore, the amount of movement can be obtained to a higher degree of accuracy compared to an instance in which only one scale-detecting means is present. The calculation performed in this instance is a simple one in which merely an average value is obtained, and can be performed in a short period of time. Furthermore, the computation means outputs the result of this calculation as a single signal. Therefore, this output signal can be used to perform feedback control. The moving body can thereby be moved by a desired amount of movement to a high degree of accuracy.

In the motion control system according to the present invention, the computation means preferably has software for performing interpolation on the signal outputted from the scale-detecting means. A configuration of such description makes it possible to perform a computation process using a plurality of scale-detecting means at a higher speed compared to an instance in which an interpolation unit is configured using dedicated hardware; to realize feedback control; and to control the amount of movement to a high degree of accuracy.

Also, having the interpolation be software-enabled as opposed to hardware-enabled makes it possible to minimize the cost of the entire motion control system.

In the motion control system according to the present invention, the computation means preferably comprises a computer having a configuration in which a program and data are stored in separate cache memories, and a program bus and a data bus are separately provided. A configuration of such description makes it possible to achieve an even faster computation process. A computer of such configuration is known as a Harvard-type computer, and is considered distinct from a Neumann-type computer.

The computation means preferably performs computation control using a reduced instruction set computer (RISC)-type central processing unit (CPU). A RISC-type CPU processes commands that are simpler than a complex instruction set computer (CISC)-type CPU, and an even faster computation process can be achieved. Some CISC-type CPUs are also able to perform high-speed processing, and a CISC-type CPU of such description can also be used.

In the motion control system according to the present invention, the time between the computation means receiving the output from the scale-detecting means and the computation means outputting the calibrated angle data signal is preferably 20 µs or less. A configuration of such description makes it possible to realize full closed loop control in a reliable manner.

In the motion control system according to the present invention, it is possible to use a configuration in which the moving body is a rotating body; the scale is provided directly around the moving body or provided on an object that moves integrally with the moving body; and the scale-detecting means is provided around the rotating body. A configuration of such description makes it possible to control the rotation angle of the rotating body.

In the motion control system according to the present invention, it is possible to use a configuration in which the scale-detecting means include, as a single group, n scale-detecting means arranged at regular intervals (where n is 2, 3, 5, or another prime number); have a data storage table in which error components of a higher order than an nth-order error component of the group are stored; and combine angle data obtained by the computation means with an error component stored in the data storage table.

A configuration of such description makes it possible to factor in higher-order Fourier error components and obtain a highly accurate angle data.

In the motion control system according to the present invention in which the data storage table of the above description is used, the scale-detecting means can be configured so as to include a plurality of groups of scale-detecting means with different values of n. It thereby becomes possible to detect error of an even higher order.

Each of the groups of the scale-detecting means may have at least one scale-detecting means that also belongs to another group. It thereby becomes possible to reduce the number of scale-detecting means, save space, and reduce cost.

In the motion control system according to the present invention, the periodic wave signal may be an AB signal that includes an A-phase, which is a cosine wave; and a B-phase, which is a sine wave; or an ABZ signal that includes, in addition to the A-phase and the B-phrase, a Z-signal that represents a reference position.

In view of the fact that an ideal cosine wave and an ideal sine wave are shifted from each other by 90° in phase, the periodic wave signal may be an AB signal that includes an A-phase and a B-phase which are waves having different phase from each other.

Next, an X-ray measurement apparatus according to the present invention is an X-ray measurement apparatus having a goniometer for causing an X-ray source and an X-ray detector to rotate by a predetermined angle; wherein the goniometer has a first motion control system configured from the motion control system according to any of the configurations described above, and a second motion control system configured from the motion control system according to any of the configurations described above, the moving body included in the first motion control system and the second motion control system is a rotary stage that rotates about an axis passing through the rotary stage; the X-ray source is supported by the rotary stage included in the first motion control system; and the X-ray detector is supported by the rotary stage included in the second motion control system.

According to the X-ray measurement apparatus of such description, interpolation is performed using software, and the computation process using a plurality of the scale-detecting means is performed at a high speed, therefore making it possible to realize feedback control in effect, and to control the rotation angle of the rotary stage to a high degree of accuracy.

Also, interpolation is performed using software, instead of hardware, making it possible to minimize the cost of the entire X-ray measurement apparatus.

BRIEF DESCRIPTION OF THE DRAWINGS

FIG. 1 is a block diagram showing an embodiment of the motion control system according to the present invention;

FIG. 14 is a block diagram showing a conventional example of the motion control system according to the present invention.

DESCRIPTION OF THE PREFERRED EMBODIMENTS

Figure 2A:
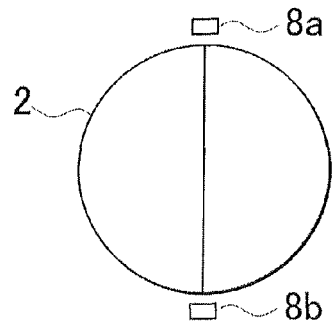
FIG. 2 is a drawing showing a plurality of configurations of arrangement of scale-detecting means.

A motion control system according to the present invention will now be described based on embodiments. The motion control system according the present invention is in no way limited to the following embodiments. The following descriptions are provided with reference to the accompanying drawings. In order to show characteristic portions in a manner that is easy to understand, constituent elements may be shown in the drawings at a scale that is different from reality.

First Embodiment of Motion Control System

FIG. 1 shows an embodiment of a motion control system according to the present invention. This motion control system 1 is an apparatus for controlling a rotation angle (i.e., amount of movement) of a rotary stage 2, which functions as a moving body and which rotates about an axis X0, to a high degree of accuracy. The axis X0 extends in a direction orthogonal to the plane of the diagram (i.e., in a direction that penetrates the plane of the diagram) in FIG. 1. A plurality of scales (i.e., calibrations) 3 are provided at regular intervals around the rotary stage 2 as shown in the partially expanded diagram (a). The scales 3 are formed using a marking apparatus having an appropriate configuration. In the present embodiment, the scales 3 are formed directly on the rotary stage 2, which functions as the moving body. Alternatively, an encoder disc may be connected to the rotary stage 2, and scales provided on the encoder disc.

<Overall Configuration of Motion Control System>

The motion control system 1 comprises a servo motor 4, which functions as moving-body-driving means, and which is adapted for driving and causing the rotation of the rotary stage 2 functioning as the moving body rotary stage; a servo amplifier 6, which functions as control means for controlling the rotation angle of the servo motor 4; and a controller 7 for feeding an angle instruction signal S0 to the servo amplifier 6. The angle instruction signal S0 is a signal for indicating the angle by which the rotary stage 2 is to rotate about the axis X0.

The motion control system 1 also has a plurality (8 in the present embodiment) of reading heads 8a through 8h, which function as scale-detecting means for reading the scales 3 on the rotary stage 2; and a data processing part 9, which functions as computation means for receiving output from each of the reading heads and outputting a rotation angle signal S1. The rotation angle signal S1 is a signal showing the rotation angle of the rotary stage 2; and is an angle signal after computation processing, obtained by performing a predetermined calculation on a measured rotation angle that has been detected by each of the reading heads 8a through 8h based on the scales 3.

Each of the reading heads 8a through 8h is configured from, e.g., a reflection-type light sensor having a configuration in which light is emitted from a light-emitting element, reflected by the scales 3, and received by a light-receiving element. It shall be apparent that a transmission-type light sensor or another sensor having an appropriate structure may also be used according to the format of the scales 3.

The rotation angle signal S1 after computation processing by the data processing part 9 is sent to a control signal input terminal of the servo amplifier 6. The servo amplifier 6 establishes as a target value the angle instruction signal S0 sent from the controller 7, establishes as a control condition value the rotation angle signal S1 after computation processing, and feeds a driving signal to the servo motor 4. The rotary stage 2 thereby rotates, e.g., in the direction shown by arrow A, by an angle that is correctly established following computation processing.

<Full Closed Loop Control>

Rotation control methods that are generally known include open-loop control, semi closed loop control, and full closed loop control. Open-loop control is a method in which an input pulse fed to a pulse motor (i.e., a stepping motor), which functions as a driving source, is controlled, thereby controlling the amount of movement (e.g., rotation angle) of a moving body driven by the pulse motor.

Semi closed loop control is a method in which, instead of information relating to the amount of movement (e.g., rotation angle) of the moving body (e.g., rotating body) being directly obtained, rotation information is obtained from an output shaft of a servo motor, which functions as a driving source, or information relating to the amount of movement is obtained from a power transmission system linking the output shaft of the servo motor to the moving body; the information relating to the amount of movement is fed back to the servo motor; and the amount of movement of the moving body is controlled.

Full closed loop control is a method in which the amount of movement of a moving body (e.g., a rotary stage) to be controlled is directly detected; the information relating to the amount of movement is fed back to the servo motor; and the amount of movement of the moving body is controlled.

In the present embodiment, the rotation angle of the rotary stage 2 to be controlled is directly detected using the reading heads 8a through 8h; the rotation angle information thus detected is fed back to the servo amplifier 6; and the rotation angle of the rotary stage 2 is controlled. Therefore, in the present embodiment, the control that is performed is based on full closed loop control.

<Head Layout>

FIG. 1 is a schematic illustration of the state of arrangement of the eight reading heads 8a through 8h. In reality, the reading heads 8a through 8h are arranged around the rotary stage 2 according to a combination of arrangements of reading heads arranged in regular intervals, the number of reading heads in each arrangement being 2, 3, and 5, which are prime numbers as shown in FIG. 2F. Specifically, the reading heads 8a through 8h are arranged in a combination of three groups: (1) a group comprising two heads 8a, 8f arranged at regular angular intervals of 180°; (2) a group comprising three heads 8a, 8d, 8g arranged at regular angular intervals of 120°; and (3) a group comprising five heads 8b, 8c, 8e, 8g, 8h arranged at regular angular intervals of 72°.

Figure 3:
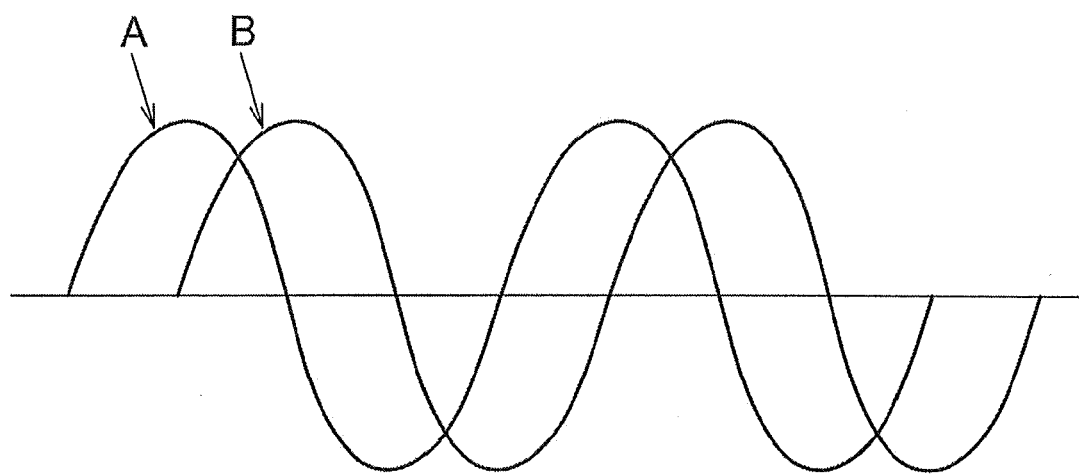
FIG. 3 is a graph showing an example of periodic wave signals detected by the scale-detecting means.

Using a head arrangement of such description and performing the calculation for angle calibration as described further below makes it possible to perform a calibration up to a high-order Fourier component excluding integer multiples of the lowest common multiple of the number of heads arranged at regular angular intervals, and to detect the rotation angle to a high degree of accuracy. Each of the reading heads 8a through 8h outputs periodic wave signals with a phase difference of 90° with respect to each other; the wave signals comprising an A-phase wave, which is a cosine wave, and a B-phase wave, which is a sine wave; as shown in FIG. 3. The scales 3 shown in FIG. 1(a) include a mark used to generate a reference signal. A head 8a through 8h that reads the reference mark outputs a reference angle signal. This reference angle signal shall hereafter be referred to as a Z-signal.

<Data Processing Part>

Figure 4:
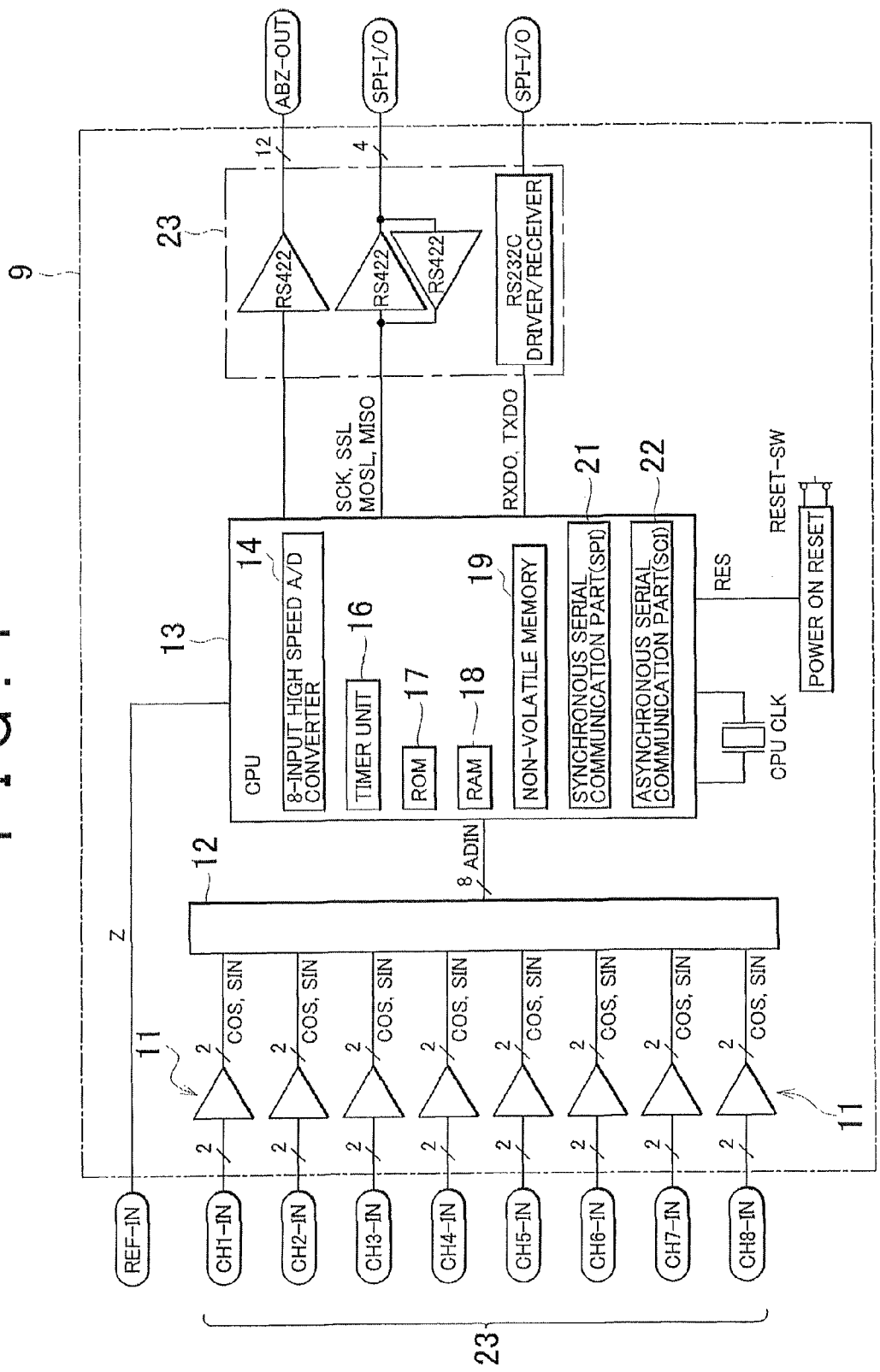
FIG. 4 is a block diagram showing an internal configuration of a data processing part, which is a major part of FIG. 1.

The data processing part 9 shown in FIG. 1 has sixteen differential amplifiers 11 (eight of which are shown in FIG. 4), an analog selector 12, and a one-chip-type CPU 13, as shown in FIG. 4. In the present embodiment, an SH Microcomputer, which is a 32-bit RISC microcomputer manufactured by Renesas Electronics Corporation, is used as the 1-chip type CPU 13. Although a 1-chip type CPU 13 is used in the present embodiment, an application specific integrated circuit (ASIC) or a large-scale field programmable gate array (FPGA) may be used instead. Nevertheless, the 1-chip type CPU is the most inexpensive of those listed above, and beneficial in terms of cost.

The 1-chip type CPU 13 is internally provided with functional modules comprising an 8-input high-speed analog-to-digital (A/D) converter 14; a timer unit 16; read-only memory (ROM) 17, random access memory (RAM) 18, non-volatile memory 19; a synchronous serial communication part (SPI) 21; and an asynchronous serial communication part (SCI) 22. Specifically, the 1-chip type CPU 13 is integrated into a single large scale integrated circuit (LSI), other than a driver/receiver 23 for the data processing part, and the analog amplifiers 11.

Known computer configurations include Harvard type and Neumann type. A Harvard-type computer is a computer having a configuration in which a program bus and a data bus are separate, and cache memory for storing programs and cache memory for storing data are separate. In contrast, a Neumann-type computer is one having a configuration in which a program bus and a data bus are shared, and programs and data are stored in the same memory. A Harvard-type computer has a simple configuration and is able to perform computation processes at a high speed, and is therefore suitable for the present embodiment, which aims to perform calculation in real time.

Sensor output 23 outputted along 8 channels from the eight reading heads 8a through 8h shown in FIG. 1 is amplified by the sixteen differential amplifiers 11, selected by the analog selector 12 to a limit of eight inputs, and inputted into the 1-chip type CPU 13.

<Software>

Software for performing interpolation, and software for calculating the calibrated angle data based on the measured angle data detected by the eight reading heads 8a through 8h are stored in the ROM 17 in the 1-chip type CPU 13 shown in FIG. 4. Interpolation is a process in which the frequency of each of the A-phase and B-phase periodic wave signals shown in FIG. 3 outputted from the reading heads 8a through 8h is subjected to an n-fold increase (where n is an integer). This interpolation is performed in order to increase the reading accuracy. A description will now be given for interpolation software and angle computation software.

<Interpolation>

Figure 5:
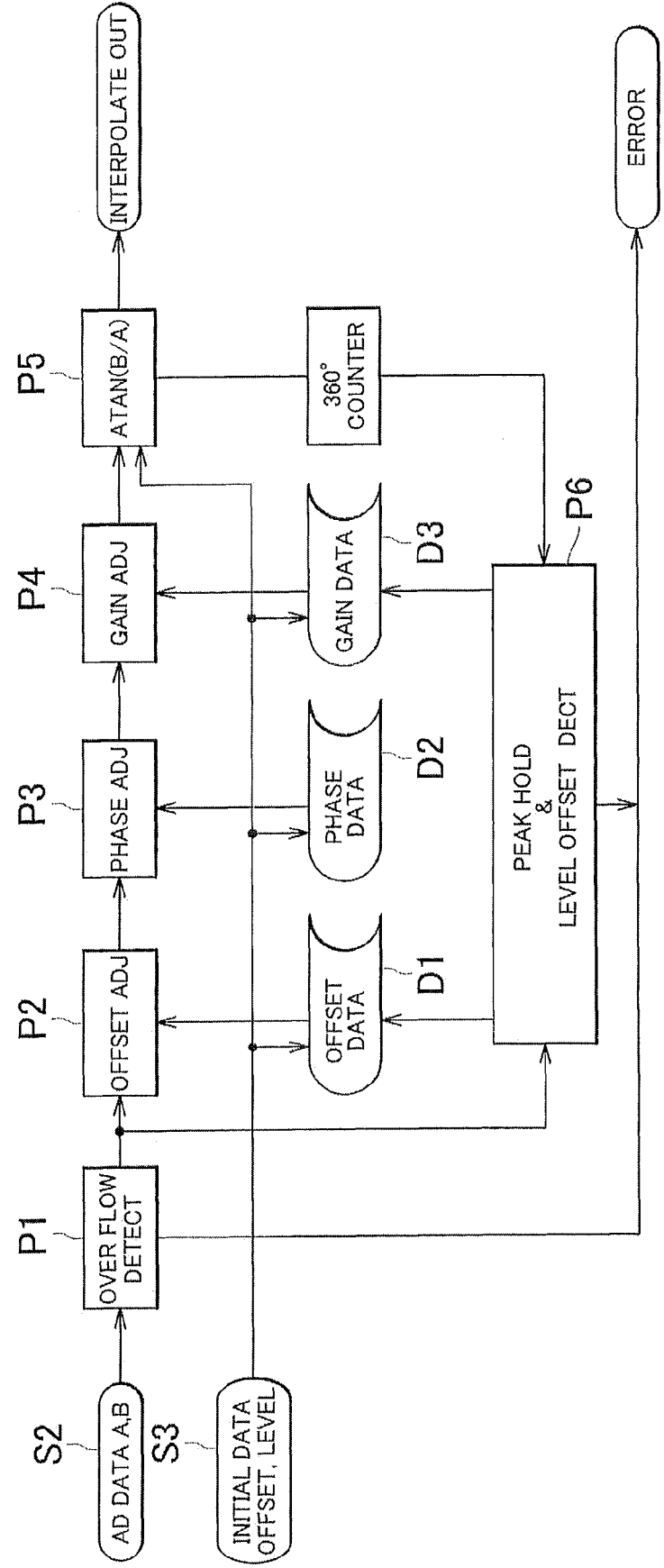
FIG. 5 is a block diagram functionally illustrating interpolation, which is major software realized by the circuit shown in FIG. 4.

In the present embodiment, the interpolation is performed completely using software processing. FIG. 5 shows functions of the interpolation software as a block diagram. FIG. 5 shows the flow for a single input, but a plurality (a maximum of eight in the present embodiment) are performed by time division overall.

Input data S2 for the interpolation comprises two items of digital data, obtained as a result of performing analog-to-digital (A/D) conversion on A-phase and B-phase analog data with a phase difference of 90° with respect to each other (see FIG. 3) using the A/D converter 14 (see FIG. 4). The inputted data is subjected to overflow detection P1. This overflow detection P1 is detection of a state of excessive input that exceeds the scope of conversion by the A/D converter.

In interpolation, a difference in gain between the sine input and the cosine input; offset; and the phase difference between the sine input and the cosine input are extremely important in maintaining accuracy. For a 1000-fold interpolation, e.g., the difference in gain between the sine input and the cosine input must be 0.89% or less; the offset error must be 0.31% or less; and the phase difference between the sine input and the cosine input must be 0.18% or less. A process in which the above-mentioned three types of errors are calibrated is performed in steps P2 through P4. With regards to offset and gain, the plus-side and minus-side peaks of each of the sine data and the cosine data are held (step P6), and calibration is automatically performed while averaging along the time axis is performed and data renewed.

Next, arctangent processing (step P5) is performed on the sine data and the cosine data, and the interpolated angle is calculated.

In the arctangent processing, the phase angle is calculated using the following formula $$\theta = \tan^{-1}(B/A)$$

where A=cosine data and B=sine data.

For example, for 1000-fold interpolation, the calculation results are normalized to a unit obtained by dividing 360° by 1000, and outputted. Error detected in the overflow detection P1 and the peak hold process P6 is outputted to the exterior.

In the arctangent processing, an arctangent value is calculated based on the value of A and the value of B according to the formula above, and is designated as the value of θ. In the software used in the present embodiment, a table of arctangents is readied in advance, and the value of θ corresponding to the value of A and the value of B is extracted from the table, instead of a formula computation of the arctangent actually being performed every time the flow is at the step in which the arctangent value is calculated. It is thereby possible to significantly reduce the processing time for arctangent processing.

In order to achieve full closed loop control in the motion control system 1 shown in FIG. 1, the time between the data processing part 9 receiving the measured angle signal from each of the reading heads 8a through 8h and the data processing part 9 computationally obtaining and outputting the calibrated angle signal S1, i.e., the system delay, must be within a predetermined time. If computation that is performed exceeds this predetermined time, it becomes impossible to perform substantive full closed loop control, due to the inertial force of the mechanical system surrounding the rotary stage 2 and other effects. Generally, full closed loop control is possible if the system delay is 20 μs or less.

In general, possible factors that define the system delay include delay due to a low-pass filter (LPF) for increasing the signal-to-noise ratio of a sine wave, and delay for performing interpolation. Delay due to a low-pass filter is normally about 10 μs. Therefore, if the time taken to perform interpolation can be limited to 10 μs or less, it becomes possible to realize a system delay of 20 μs or less at which full closed loop control is possible.

According to the conventional interpolation process using hardware shown in FIG. 14, it is difficult to limit the processing time to 10 μs or less. In the present embodiment, the interpolation is performed, using software, within the data processing part 9 configured using a microcomputer; and computation of the arctangent in the interpolation process is performed using a table. It is therefore possible to limit the time taken for the interpolation process to 10 μs or less. As a result, it is possible to limit the system delay to 20 μs or less, and to realize full closed loop control.

<Angle Computation Processing by Automatic Calibration>

Figure 6:
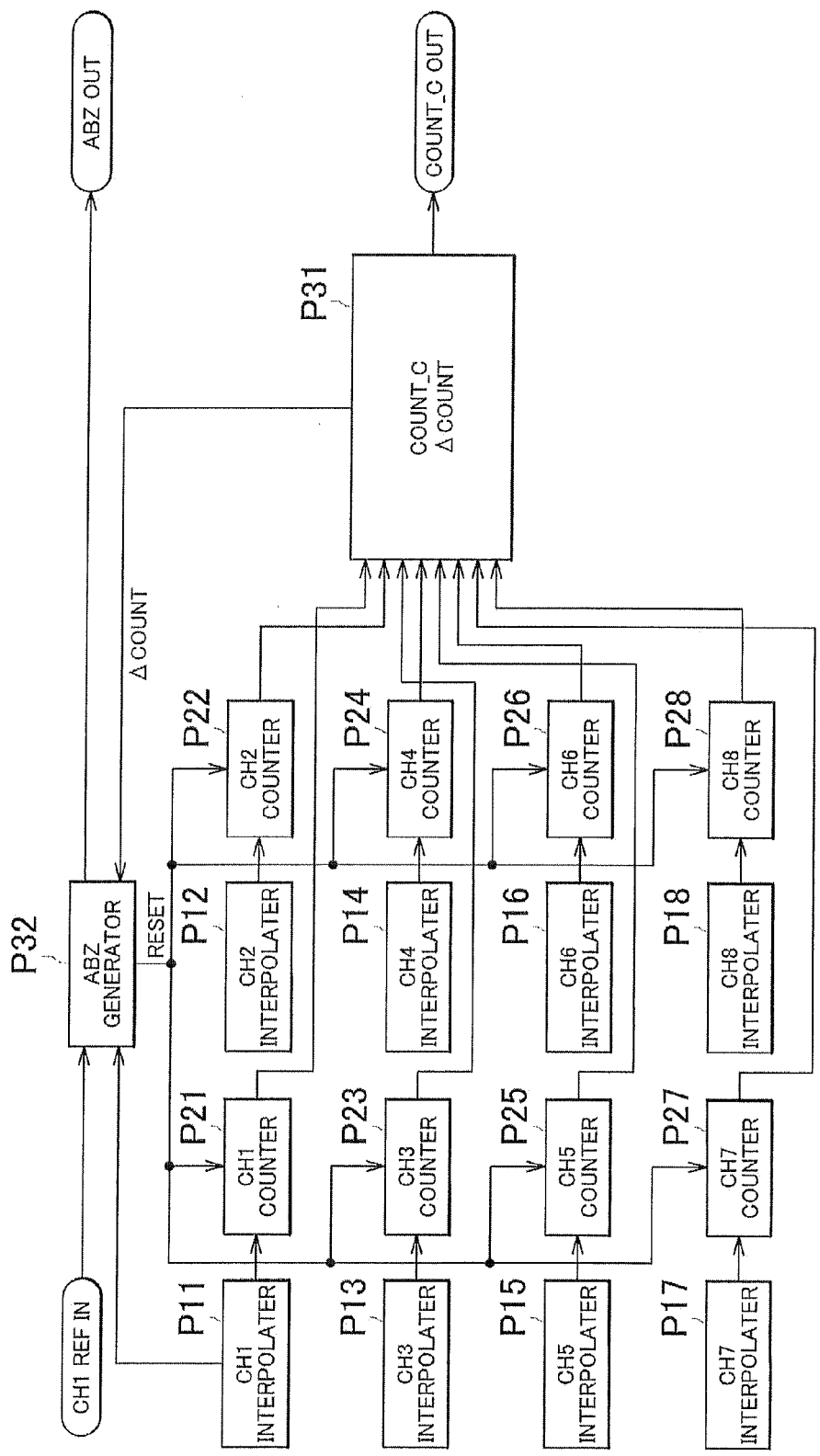
FIG. 6 is a block diagram functionally illustrating an angle computation process, which is other major software realized by the circuit shown in FIG. 4.

FIG. 6 shows functions of an angle computation process, realized using the CPU 13 (see FIG. 4), as a block diagram. In the angle computation process, each of Ch1 interpolation step P11, Ch2 interpolation step P12, Ch3 interpolation step P13, Ch4 interpolation step P14, Ch5 interpolation step P15, Ch6 interpolation step P16, Ch7 interpolation step P17, and Ch8 interpolation step P18 represents an interpolation step in relation to an output signal from the reading head 8a, 8b, 8c, 8d, 8e, 8f, 8g, and 8h shown in FIG. 2F, respectively. In the present embodiment, an arbitrary single reading head, e.g., the reading head 8a, is considered a reading head used as a reference for evaluating head positions and for resetting.

"Reading head used as a reference" described here refers to the reading head being used as a reference when evaluating the position of arrangement of each of the reading heads 8a, 8b, 8c, 8d, 8e, 8f, 8g, and 8h or when generating a reset signal, and does not refer to any single reading head being considered as a reference reading head when performing a computation process in relation to the rotation angle of the rotary stage 2.

In the present embodiment, each of the reading heads 8a, 8b, 8c, 8d, 8e, 8f, 8g, and 8h is used independently as a basis for computation, and no single reading head is defined as a basis for computation. The reference reading head according to the present embodiment may be an arbitrary reading head other than the reading head 8a.

With regards to angle data obtained by interpolation in each of the above steps, a difference in relation to the immediately preceding data is obtained and added respectively to a counter P21, P22, P23, P24, P25, P26, P27, or P28 corresponding to each of the data. The output obtained from each of the counters as a result of the addition is Count1, Count2, Count3, Count4, Count5, Count6, Count7, and Count8, respectively.

As described further above, the eight reading heads according to the present embodiment comprise a combination of three groups: a group comprising two heads 8a, 8f arranged at regular angular intervals of 180°; a group comprising three heads 8a, 8d, 8g arranged at regular angular intervals of 120°; and a group comprising five heads 8b, 8c, 8e, 8g, 8h arranged at regular angular intervals of 72°.

In the computation step P31, an average value of each of the groups is obtained; an average value of each of the resulting average values is obtained; and the following count value Count_c is calculated.

Count_c=[{(Count1+Count5)/2}+{(Count1+Count3+Count7)/3}+{(Count2+Count4+Count5+Count6+Count8)/5}]/3    (Formula 1)

A weighted average may also be obtained instead of a simple average.

The count value Count_c described above is the correct angle data for the rotary stage 2 (FIG. 1) that has been calibrated. Count_c is outputted as the rotation angle signal S1 shown in FIG. 1, and is considered a control condition value for feedback control.

All of the count values corresponding to the reading heads are reset by a Z-signal from a specific reading head, e.g., the reading head 8a corresponding to Count1.

A difference Δcount between Count1 of the reading head 8a and the calibrated Count_c, i.e., the amount of calibration, is obtained by $$\Delta count = Count\_c - Count1$$

This difference Δcount is used when evaluating the characteristics or position of arrangement of individual reading heads.

The calibrated angle data, which is a result of the computation process according to the above-mentioned Formula 1, is outputted to the exterior. Also, the output representing the difference output Δcount with respect to the reading head 8a is sent to an ABZ generation module P32. The ABZ output thereby corresponds to a calibrated output.

Since the motion control system 1 according to the present embodiment is configured as above, in FIG. 1, the angle instruction signal S0 is transmitted from the controller 7 to the servo amplifier 6; the servo amplifier 6 transmits a driving signal to the servo motor 4 according to the angle instruction signal S0; and the rotary stage 2 is thereby driven by the servo motor 4 and caused to rotate about the axis X0 as shown by arrow A towards an indicated target angle. During this rotation, the scales 3 are read by each of the reading heads 8a through 8h, and the measured angle data is outputted by an output terminal of each of the reading heads 8a through 8h as periodic wave signals having an A-phase (i.e., a cosine wave) and a B-phase (i.e., a sine wave) such as those shown in FIG. 3. The output from each of the reading heads includes the Z-signal, which represents a reference point, i.e., a zero point.

The measured angle data from each of the reading heads is subjected to analog-to-digital conversion by the A/D converter 14 included in the CPU 13 shown in FIG. 4; subjected to an interpolation process by the interpolation software shown in FIG. 5; and subjected to, e.g., a 1000-fold frequency interpolation. Each of the measured angle data that has been subjected to interpolation is subjected to computation according to the above-mentioned Formula 1 by the computation process software shown in FIG. 6. As a result, the calibrated angle data Count_c is obtained, and Count_c is transmitted to a control signal input terminal of the servo amplifier 6 as the rotation angle signal S1 shown in FIG. 1.

The servo amplifier 6 controls the signal inputted into the servo motor 4 according to the transmitted rotation angle signal S1, and controls the rotation angle of the rotary stage 2. Thus, feedback control is performed according to a full closed loop control method, and the rotary stage 2 rotates to the desired rotation angle at a high degree of accuracy.

In the present embodiment, the time between the data processing part 9 receiving the measured angle signal from each of the reading heads 8a through 8h and the data processing part 9 outputting the calibrated angle signal S1, i.e., the system delay, is limited to 20 μs or less. Specifically, real-time angle computation process is performed. Therefore, the full closed loop control shown in FIG. 1 can be substantively realized.

According to an experiment performed by the inventors, in an instance in which feedback control is performed solely using one reading head 8a shown in FIG. 1 and using measured angle detection data (i.e., data including error) without performing angle calibration computation, an error accuracy of only $\pm(2/1000)°$ could be obtained. It was found that according to the present embodiment in which, in contrast, a real-time angle computation process is realized, whereby the correct angle data is computationally obtained from measured angle data obtained from a plurality of reading heads and feedback control is performed based on the calibrated angle data, an error accuracy of $\pm(2/10000)°$, i.e., an accuracy that is ten times greater than in a conventional instance in which the angle computation process is not performed, can be obtained.

Also, in the present embodiment, the data processing part 9 is configured using an inexpensive microcomputer, and the interpolation is realized using software in the microcomputer instead of dedicated hardware. It is therefore possible to minimize the cost of the entire motion control system.

Also, the data processing part 9 used in the present embodiment is a RISC-type, in which processing commands are simpler and with which processing can be performed at a higher speed than a CISC-type; and is a Harvard-type, in which the program bus and the data bus are separate and with which processing can be performed at a high speed. The speed of the computation process is thereby extremely high, and it is possible to achieve real-time computation process in which the system delay is 20 μs or less, therefore making real-time feedback control possible.

Second Embodiment of Motion Control System

Figure 7:
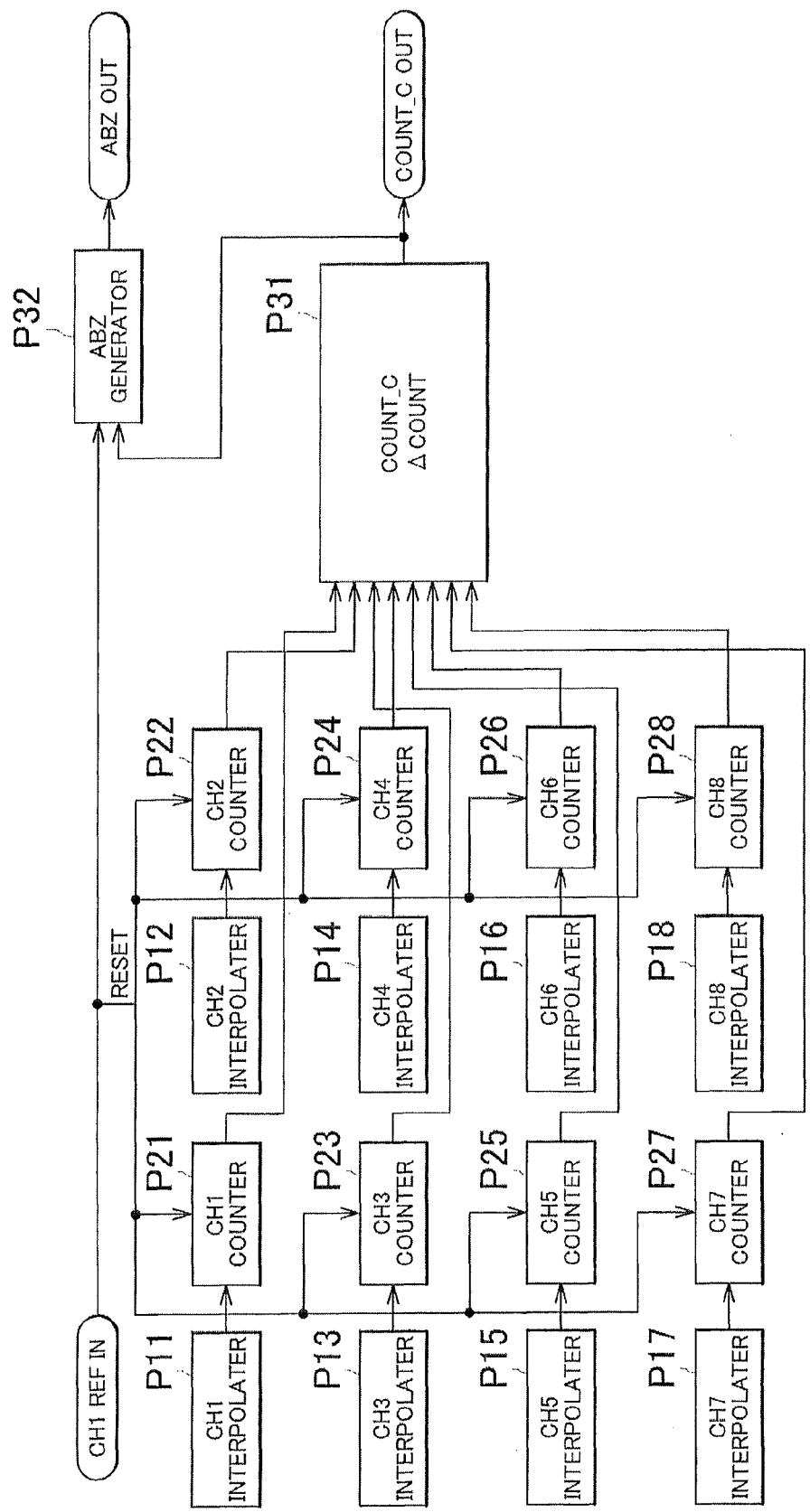
FIG. 7 is a block diagram functionally illustrating an angle computation process used in another embodiment of the motion control system according to the present invention.

In the above embodiment, in FIG. 6, the value of Δcount is obtained in computation step P31 and transmitted to the ABZ generation module P32, and a calibrated ABZ output is obtained. However, it is also possible to generate ABZ output directly from the calibrated output from the computation step P31 as shown in FIG. 7.

Third Embodiment of Motion Control System

Means for reducing the number of reading heads and calibrating for higher-order inaccuracies include the following method. Specifically, eight channels of reading heads are mounted, and the difference in calibration data for the eight channels is measured and stored in the memory. Since the capacity of the memory is finite, the difference is stored in units obtained by dividing the scale by a factor on the order of tens of thousands.

Next, the number of reading heads is reduced to, e.g., four; the calibration data for the reading heads is measured again; a difference between the calibration data for the eight channels is calculated; and the difference is stored in the non-volatile memory. If the positions of the reduced reading heads are a subset of the eight channels, the difference can be extracted simultaneously when measurement is performed. During calibration, a calibration is performed in real time using the stored data representing the difference, i.e., within a processing time in which full closed loop control can be realized, or more specifically, within a time of 20 μs or less.

Fourth Embodiment of Motion Control System

In the embodiment described above, eight reading heads 8a through 8h are arranged around the rotary stage 2 according to a combination of arrangements of reading heads arranged in regular intervals, the number of reading heads in each arrangement being 2, 3, and 5, which are prime numbers as shown in FIG. 2F. In the present embodiment, four reading heads are used instead of eight. With regards to the arrangement of the four reading heads, as shown in FIG. 2C, the four reading heads 8a through 8d are arranged around the rotary stage 2 according to a combination of arrangements of reading heads arranged in regular intervals, the number of reading heads in each arrangement being 2 and 3, which are prime numbers. Specifically, the reading heads 8a through 8d are arranged in a combination of two groups: a group comprising two heads 8a, 8c arranged at regular angular intervals of 180°; and a group comprising three heads 8a, 8b, 8d arranged at regular angular intervals of 120°.

The basic overall configuration of the motion control system used in the present embodiment is identical to the configuration shown in FIG. 1. However, the number of the reading heads is reduced from eight to four, or four of the eight reading heads are used. Also, the basic configuration within the data processing part 9 is identical to the configuration shown in FIG. 4. However, in the present embodiment, the number of the reading heads is reduced from eight to four, or four of the eight reading heads are used.

Interpolation software identical to the interpolation software used in the first embodiment shown in FIG. 5 is stored in the ROM 17. Each angle data that has been interpolated is subjected to computation processing by the angle computation process software shown in FIG. 8. Specifically, an average count value Count_c is calculated according to the following formula by a computation step P33.

$$\text{Count}\_c = [\{(\text{Count1} + \text{Count3})/2\} + \{(\text{Count1} + \text{Count2} + \text{Count4})/3\}]/2 \quad \text{(Formula 2)}$$

Fifth Embodiment of Motion Control System

In general, in an instance in which n reading heads are arranged at regular intervals and angle detection is performed, when an average of the measurements is obtained, calibration is performed, and an angle is calculated, the nth order Fourier component and higher-order Fourier components corresponding to integer multiples of n cannot be calibrated, and the corresponding Fourier components remain unknown as errors.

Figure 10:
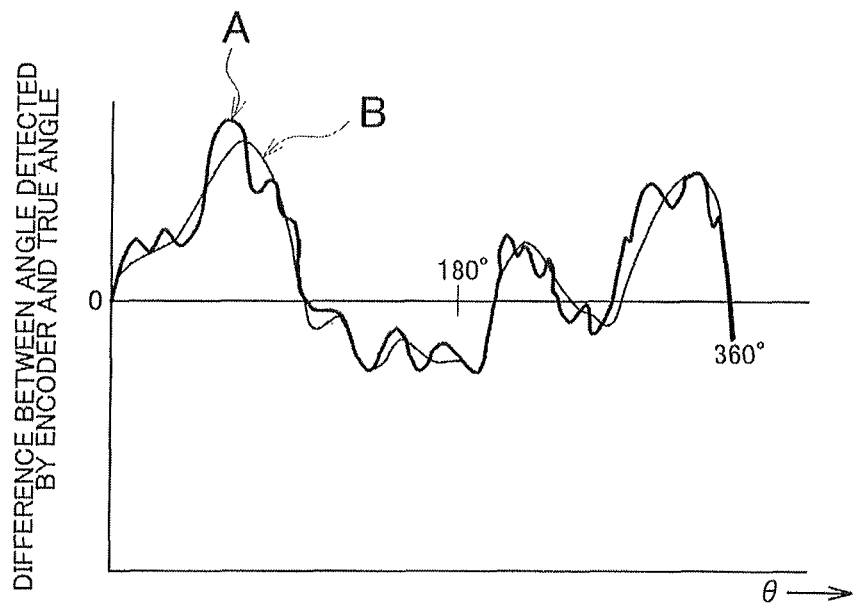
FIG. 10 is a drawing showing the error in the rotation angle in order to illustrate the embodiment shown in FIG. 9.
Figure 10:
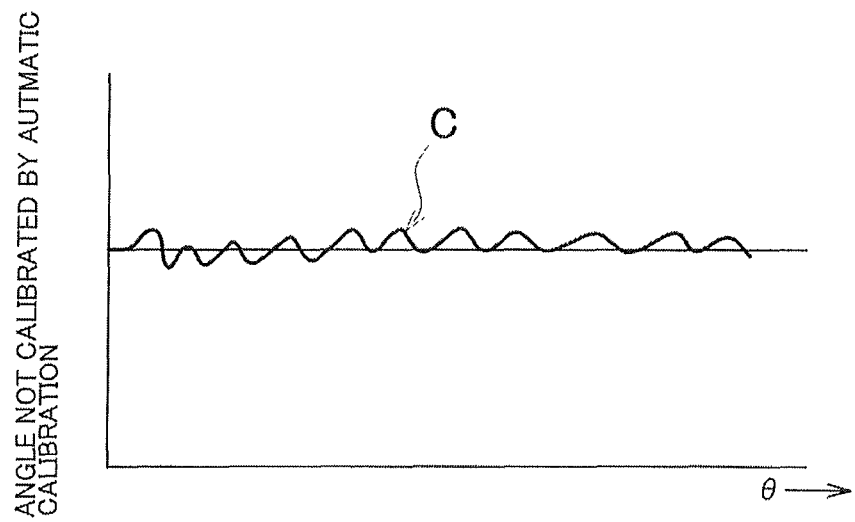

For example, when the true angle shown by the scales provided to the rotary stage is represented by curve A in the graph shown in FIG. 10, curve A occurs in accordance with formation error when the scales are formed on the rotary stage. This formation error can be identified when the scales are created.

Next, curve B represents the calibrated rotation angle data when the angle is detected in, e.g., computation step P31 shown in FIG. 6 using scales created as described above, e.g., using five reading heads arranged in regular intervals. Curve B and curve A generally include portions that do not match. In other words, curve A includes error components.

Extracting only these error components results in Curve C. The error such as that shown by curve C occurs as a result of the fifth-order Fourier component and its corresponding higher-order (e.g., $10^{th}$ order, $15^{th}$ order, etc.) Fourier components remaining without being calibrated. Curve C can be obtained by performing an actual measurement in advance.

In the present embodiment, motion control systems, respectively comprising 1 through n reading heads arranged around the rotary stage 2 at regular angular intervals, are individually created; calibration data such as curve C shown in FIG. 10 is obtained with respect to individual motion control systems; and the calibration data is stored as a calibration table in the non-volatile memory 19 shown in FIG. 4 for each value of n.

Figure 9:
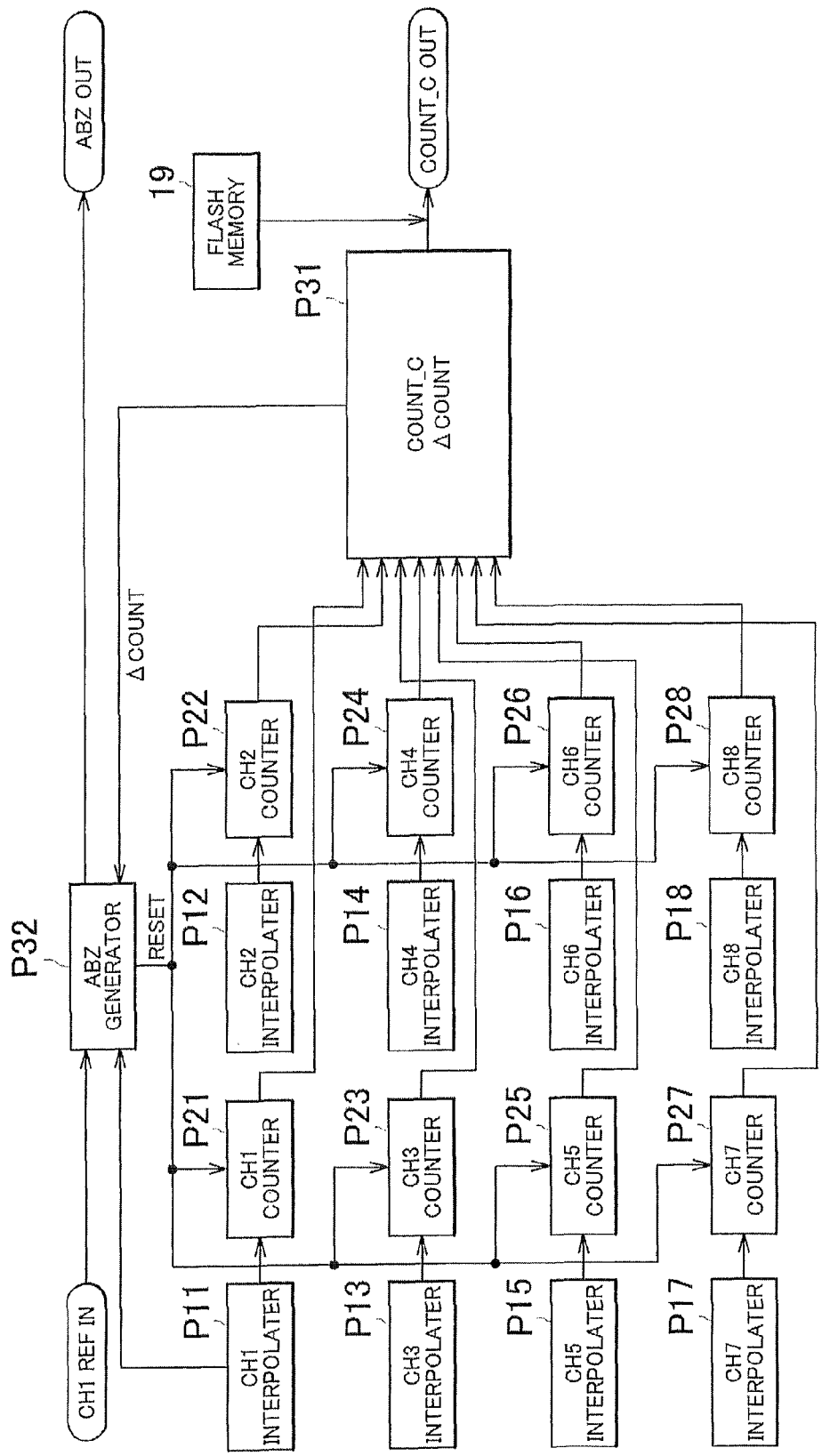
FIG. 9 is a block diagram functionally illustrating an angle computation process used in another embodiment of the motion control system according to the present invention.

Next, predetermined computation is performed and Count_c (i.e., curve B) is obtained in computation step P31 shown in FIG. 9. Then, calibration data for the corresponding value of n is read from the calibration table stored in the non-volatile memory 19, and calibration data and Count_c are combined, whereby it is possible to obtain an angle signal that has been subjected to absolute calibration in which higher-order error components are factored in. The rotation angle can be controlled according to this calibrated angle signal. In this instance, it is possible to perform rotation control to an extremely high degree of accuracy.

Figure 2B:
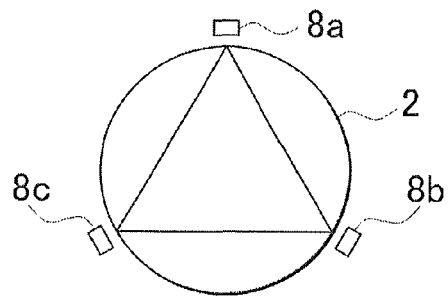
Figure 2C:
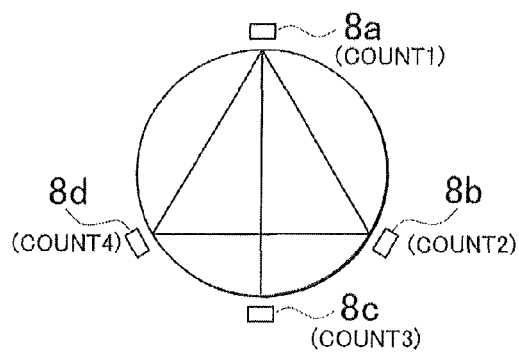
Figure 2D:
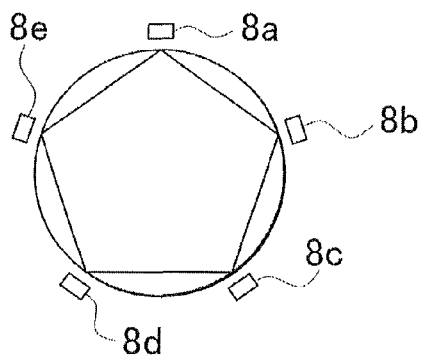
Figure 2E:
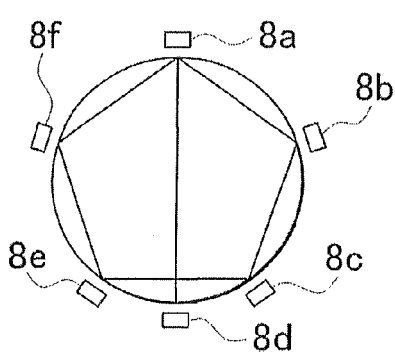
Figure 2F:
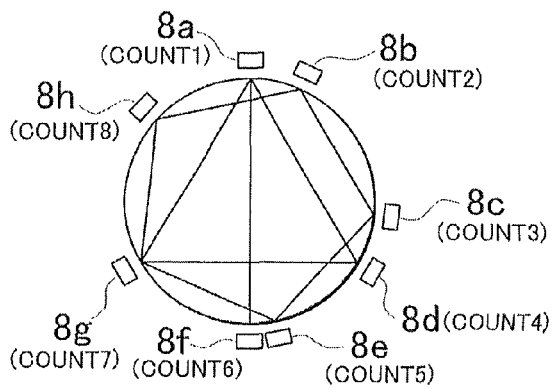

In an instance in which two reading heads are arranged at equiangular intervals, such as in FIG. 2A, calibration data for n=2 is used; in an instance in which three reading heads are arranged at equiangular intervals, such as in FIG. 2B, calibration data for n=3 is used; in an instance such as in FIG. 2C in which four reading heads are arranged at angular intervals, calibration data for n=2 and n=3 are used; in an instance in which five reading heads are arranged at equiangular intervals, such as in FIG. 2D, calibration data for n=5 is used; in an instance such as in FIG. 2E in which six reading heads are arranged at angular intervals, calibration data for n=2 and n=5 are used; and in an instance such as in FIG. 2F in which eight reading heads are arranged at angular intervals, calibration data for n=2, n=3, and n=5 are used.

In the instance shown in FIG. 2C, a single reading head 8a is a reading head that is shared between the group having two reading heads and the group having three reading heads. However, a configuration is also possible in which no reading head is shared between each of the groups. In such an instance, the final number of reading heads is five. In the instance shown in FIG. 2F, the reading head 8a is shared between the group having two reading heads and the group having three reading heads; and the reading head 8g is shared between the group having three reading heads and the group having five reading heads.

Setting a configuration in which one or more reading heads are shared between a plurality of groups makes it possible to reduce the number of reading heads to be used, and is therefore beneficial in terms of space and is also beneficial in terms of cost.

Sixth Embodiment of the Motion Control System

Figure 11:
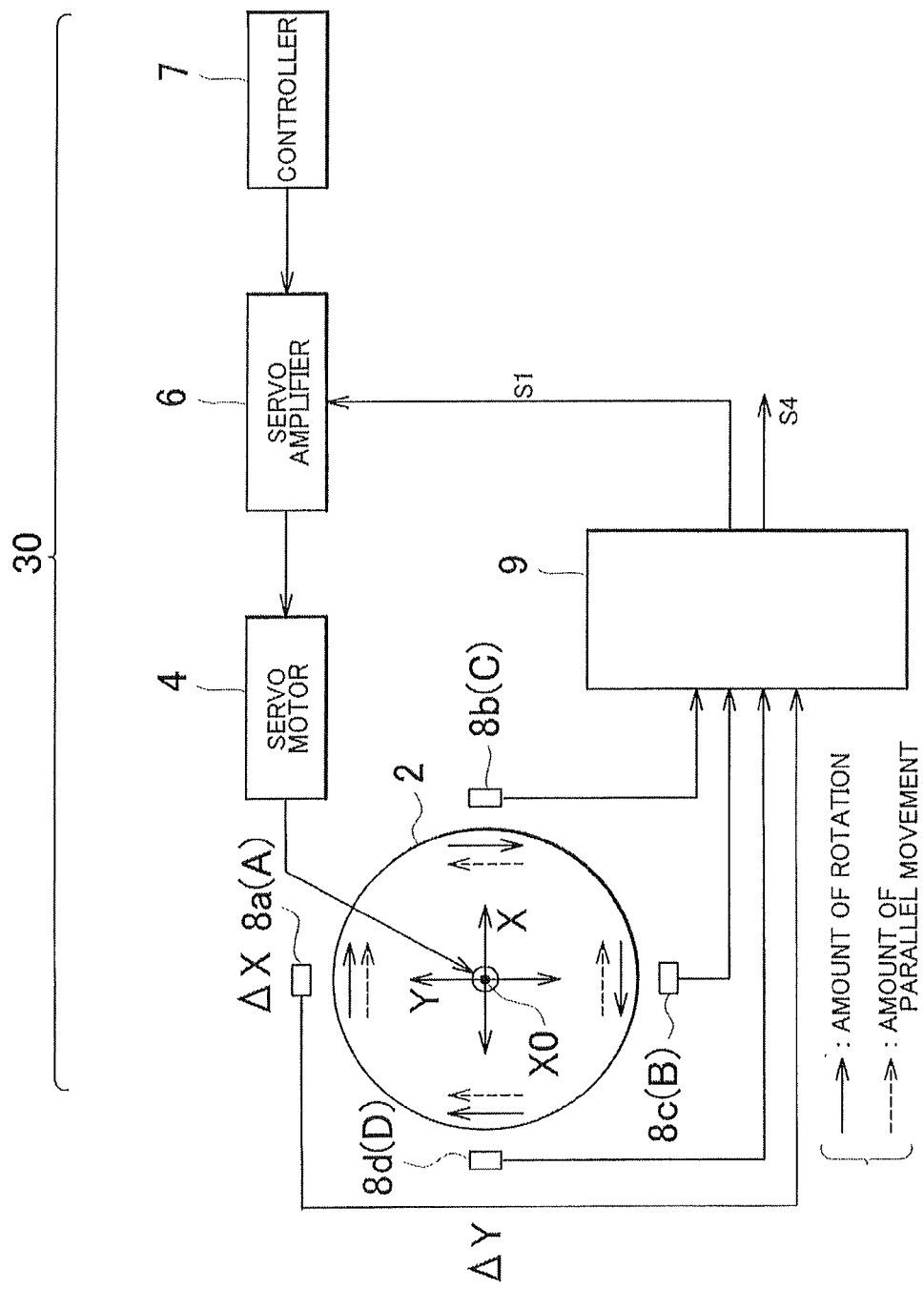
FIG. 11 is a block diagram showing another embodiment of the motion control system according to the present invention.

FIG. 11 shows another embodiment of the motion control system. The motion control system 30 according to the present invention has, in addition to a function of controlling the motion of the rotary stage 2 so that the rotation angle of the rotary stage 2 is a given angle as described above, a function for detecting an amount of deflection of a rotation axis of the rotary stage 2. This will be described in detail below.

Figure 8:
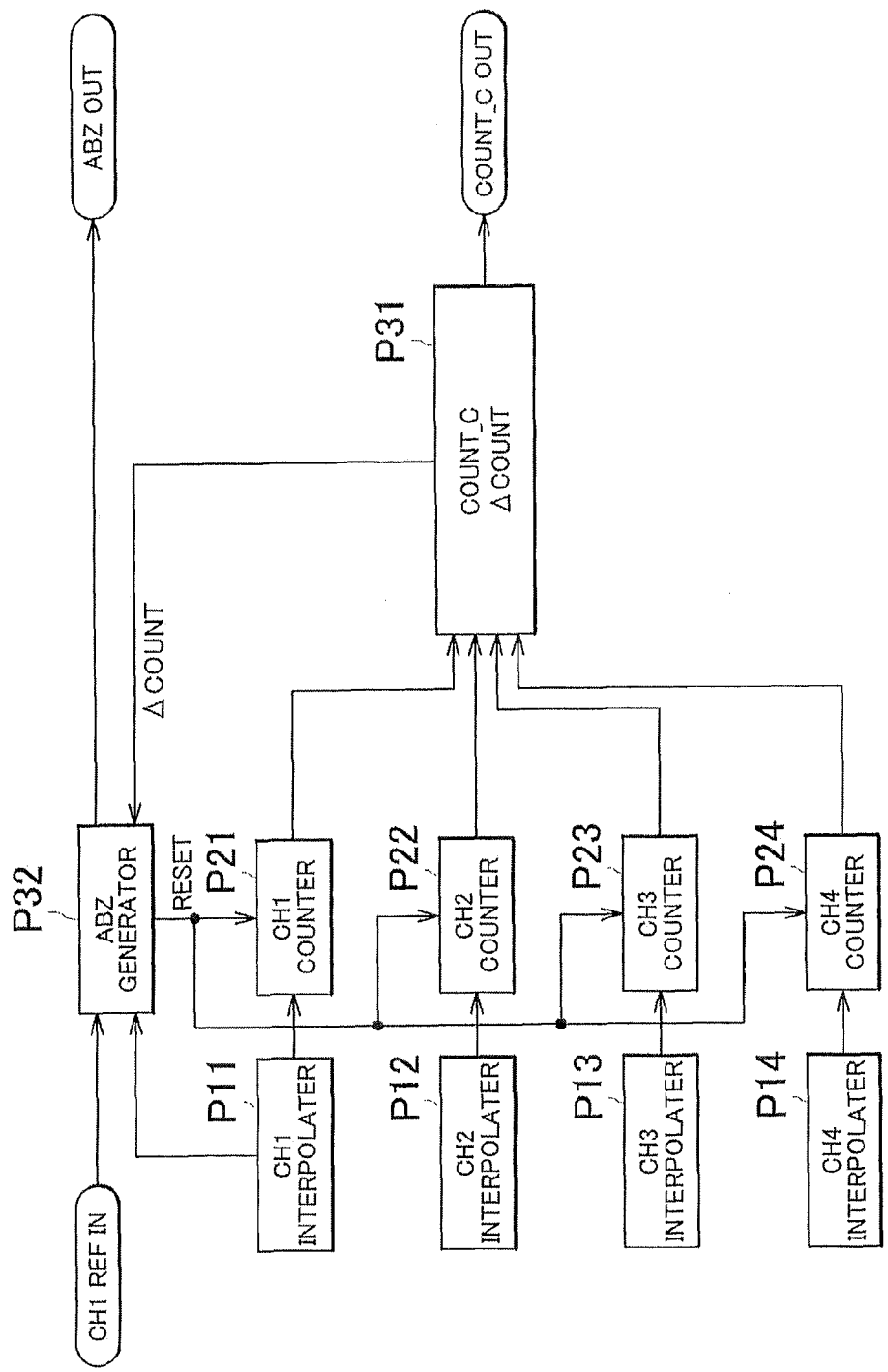
FIG. 8 is a block diagram functionally illustrating an angle computation process used in another embodiment of the motion control system according to the present invention.

A plurality (four in the present embodiment) of reading heads 8a, 8b, 8c, and 8d are arranged at regular angular intervals around the rotary stage 2, which functions as a moving body. The interpolation described using FIG. 5 and the angle computation process shown in FIG. 8 are performed using the reading heads.

Next, when A represents the value detected by the reading head 8a; B represents the value detected by the reading head 8c, which is disposed opposite the reading head 8a; C represents the value detected by the reading head 8b; and D represents the value detected by the reading head 8d, which is disposed opposite the reading head 8b, each of a displacement amount ΔX in the lateral direction (i.e., horizontal direction) and a displacement amount ΔY in the upright direction (i.e., vertical direction) is detected using the following formulae.

$$\Delta X = (A - B)/2 \quad \Delta Y = (C \Delta D)/2 \quad \text{(Formula 3)}$$

In an instance in which the rotary stage 2 is rotating, all of the reading heads 8a, 8b, 8c, and 8d detect the amount of movement in the same direction. In contrast, if a parallel deflection is present in the center axis X0, the detected value of the reading head 8a and the detected value of the reading head 8b, which are disposed opposite each other in the upright (Y) direction, will be in opposite directions with respect to each other. Also, the detected value of the reading head 8b and the detected value of the reading head 8d, which are disposed opposite each other in the lateral (X) direction, will also be in opposite directions with respect to each other. Therefore, for both the upright (Y) direction and the lateral (X) direction, subtracting the amount of deviation A, B, C, and D and dividing by two as shown in Formula 3 cancels out the rotation amount, and makes it possible to obtain the amount of parallel deflection. Thus, in addition to it being possible to output accurate rotation angle data S1, it also becomes possible to output a center deflection amount S4 of the axis.

Example of Modification

Figure 12:
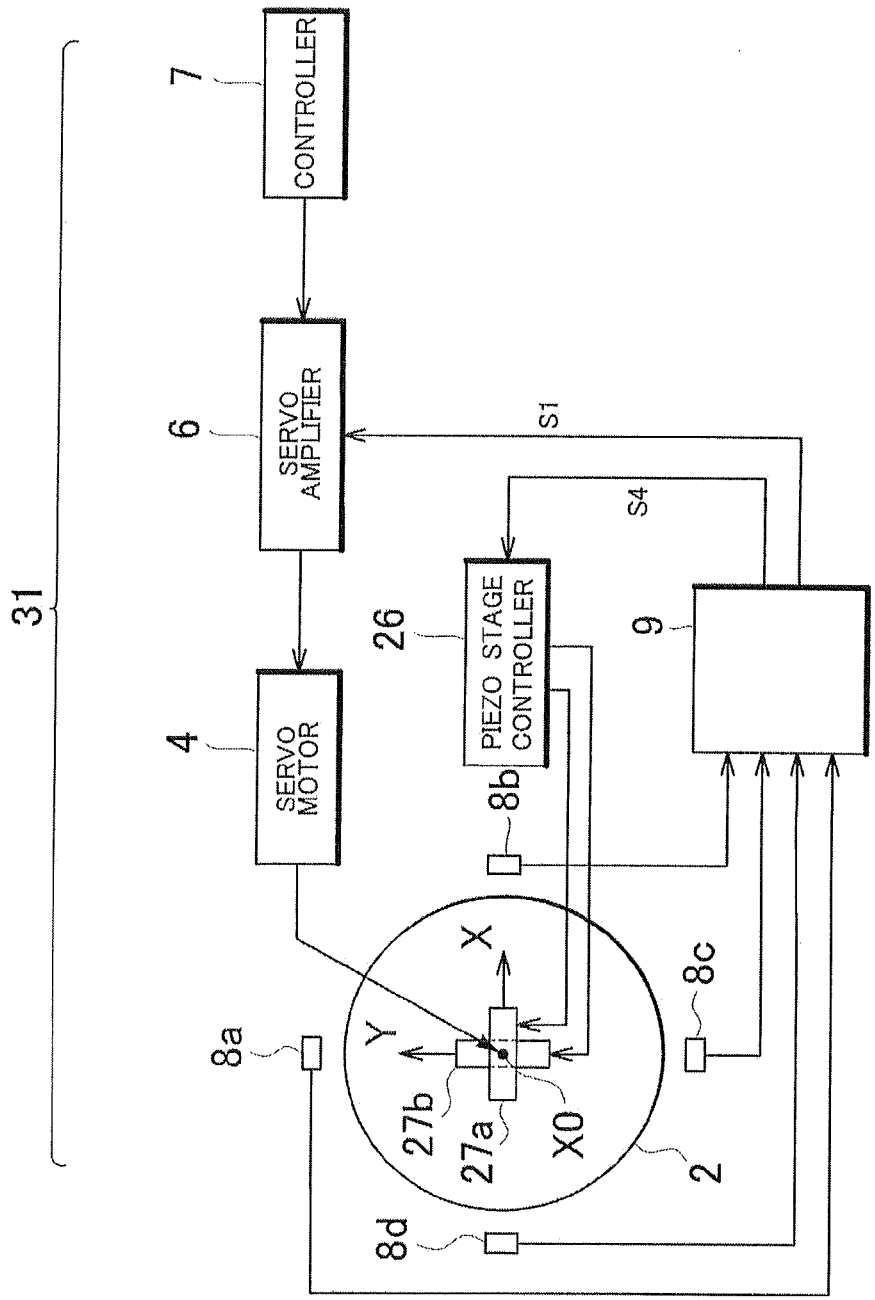
FIG. 12 is a block diagram showing another embodiment of the motion control system according to the present invention.

The data S4 representing the amount of center deflection (i.e., the amount of parallel deflection) of the axis, obtained as described above, can be transmitted to a piezo stage controller 26, as in a motion control system 31 shown in FIG. 12. The piezo stage controller 26 individually controls the operation of an x-direction piezo actuator 27a and a y-direction piezo actuator 27b mounted on the rotary stage 2. Each of the piezo actuators 27a, 27b is an element for controlling a voltage applied to a piezo element (i.e., a piezoelectric element) to cause a mobile member onto which the piezo element is mounted to move according to the impressed voltage.

The piezo stage controller 26, which has received a signal S4 representing the center deflection amount including the $\Delta x$ data and the $\Delta y$ data shown in the above-mentioned Formula 3, transmits a signal for supplementing $\Delta x$ to the x-direction piezo actuator 27a, and transmits a signal for supplementing $\Delta y$ to the y-direction piezo actuator 27b. It thereby becomes possible to calibrate for the center deflection of the rotary stage 2 using the piezo stage controller 26 and the piezo actuators 27a, 27b in real time. Real time in this instance refers to a time in which full closed loop control can be realized using the servo amplifier 6 based on the rotation angle data outputted from the reading heads 8a through 8d, or specifically, a time of 20 μs or less.

Means for causing the rotary stage 2 to move by a minute distance in order to factor in the axis deflection are not limited to the means described above in which piezo actuators are used; an appropriate configuration can be used according to purpose or requirement.

First Embodiment of X-Ray Measurement Apparatus

Figure 13:
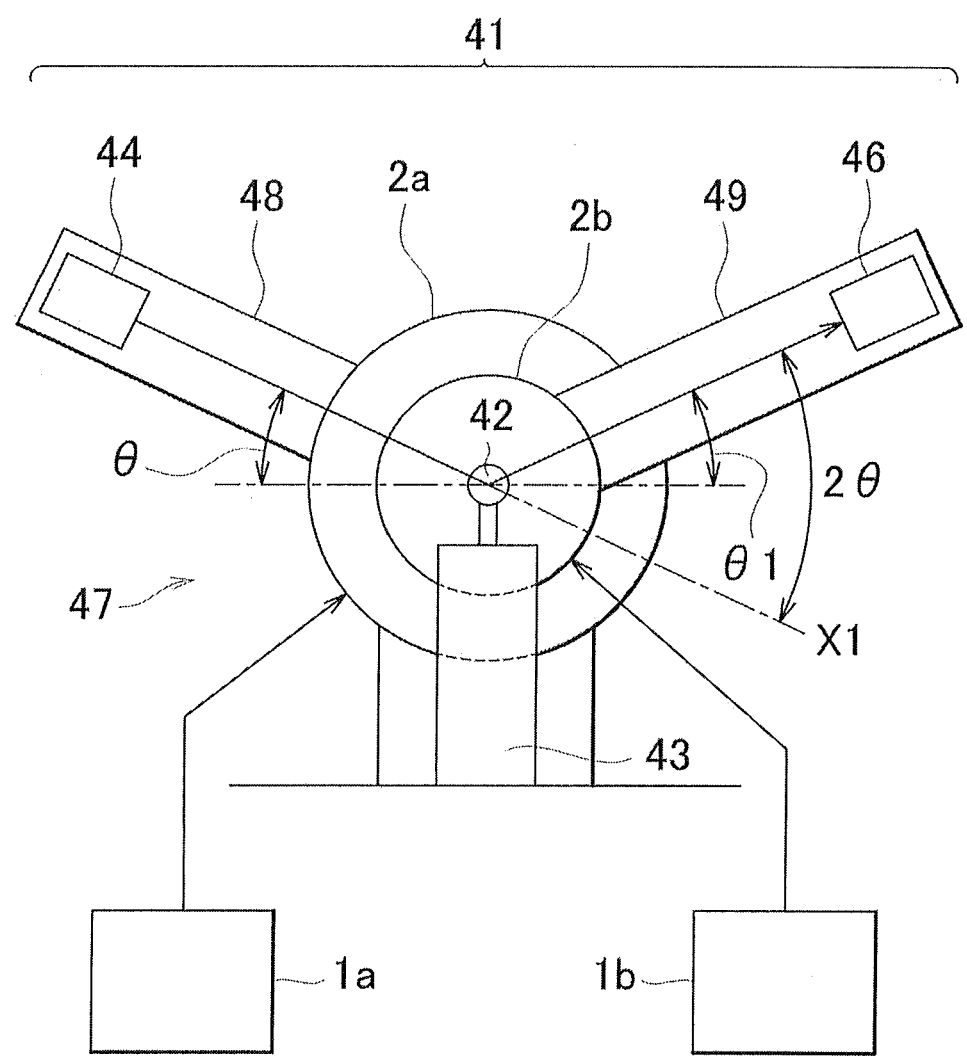
FIG. 13 is a front view showing an embodiment of an X-ray measurement apparatus according to the present invention.

FIG. 13 shows an embodiment of a X-ray measurement apparatus according to the present invention. This X-ray measurement apparatus 41 has a specimen platform 43 for supporting a specimen 42; an X-ray tube 44 for generating X-rays that are irradiate to the specimen 42; and an X-ray detector 46 for detecting X-ray that emerges from the specimen 42, e.g., diffracted X-ray. The X-ray tube 44 and the X-ray detector 46 are supported by a goniometer 47.

The goniometer 47 controls both a visual angle $\theta$ of the X-ray tube 44 in relation to the specimen 42 and a visual angle $\theta 1$ of the X-ray detector 46 in relation to the specimen 42. Normally, $\theta = \theta 1$ in terms of absolute values. The visual angle $\theta$ of the X-ray tube 44 is an angle at which the X-rays emitted from the X-ray tube 44 are incident on the specimen 42 (i.e., an "X-ray incident angle"). The goniometer 47 changes the X-ray incident angle $\theta$ at a desired angular velocity, and controls the visual angle $\theta 1$ of the X-ray detector 46 so that an angle $2\theta$ of the X-ray detector 46 in relation to an optical axis X1 of the incident X-ray is maintained at an angle that is twice as large as the X-ray incident angle $\theta$. The angle $2\theta$ of the X-ray detector 46 in relation to the optical axis X1 of the incident X-ray is an angle at which refracted X-rays emerging from the specimen 42 can be detected. This angle $2\theta$ is therefore referred to as a diffraction angle.

The goniometer 47 has an incident-side angle-measuring part for measuring the value of $\theta$, which relates to the X-ray tube 44; and a receiving-side angle-measuring part for measuring the value of $\theta 1$, which relates to the X-ray detector 46. The incident-side angle-measuring part has a rotary stage 2a, which functions as a moving body; an incident-side arm member 48 for supporting the X-ray tube 44 extending from the rotary stage 2a; and a motion control system 1a for causing the rotary stage 2a to move (i.e., rotate) by a desired amount of movement (i.e., rotation angle).

The receiving-side angle-measuring part has a rotary stage 2b, which functions as a moving body; a receiving-side arm member 49 for supporting the X-ray detector 46 extending from the rotary stage 2b; and a motion control system 1b for causing the rotary stage 2b to move (i.e., rotate) by a desired amount of movement (i.e., rotation angle).

The configuration of the combination between the rotary stage 2a and the motion control system 1a forming the incident-side angle-measuring part is identical to the configuration of the embodiment described using, e.g., FIGS. 1, 11, and 12. The configuration of the combination between the rotary stage 2b and the motion control system 1b forming the receiving-side angle-measuring part is also identical. The above configuration makes it possible to cause each of the X-ray tube 44 and the X-ray detector 46 to rotate by a desired, angle in an extremely accurate manner. As a result, it is possible to perform X-ray diffraction measurement that is extremely reliable.

Other Embodiments

Although the present invention has been described above with reference to preferred embodiments, the present invention is not limited in scope by the above embodiments, and a variety of modifications are possible within the scope of the invention described in the claims.

In the embodiments described above, an arrangement comprising four reading heads shown in FIG. 2C and an arrangement comprising eight reading heads shown in FIG. 2F are used as configurations of the arrangement of the reading heads. However, the configuration of the arrangement of the plurality of reading heads is not limited to those described, and is set as desired according to requirement. For example, an arrangement comprising two reading heads shown in FIG. 2A, an arrangement comprising three reading heads shown in FIG. 2B, an arrangement comprising six reading heads shown in FIG. 2E, or another arrangement can be used.

In the arrangement shown in FIG. 2A, two (i.e., a prime number of) reading heads 8a, 8b are arranged at regular angular intervals of 180°. In the arrangement shown in FIG. 2B, three (i.e., a prime number of) reading heads 8a, 8b, 8c are arranged at regular angular intervals of 120°. In the arrangement shown in FIG. 2D, five (i.e., a prime number of) reading heads 8a through 8e are arranged at regular angular intervals of 72°. In the arrangement shown in FIG. 2E, two (i.e., a prime number of) reading heads 8a, 8b are arranged at regular angular intervals of 180°, and five reading heads 8a, 8b, 8e, 8f are arranged at regular angular intervals of 72°.

In the embodiments described above, the rotation angle of the rotary stage 2, which functions as a moving body, is treated as the amount of movement; and this amount of movement is controlled. However, this arrangement is not provided by way of limitation. It is also possible to limit the amount of linear movement of a linearly moving body in a mechanical system for converting a rotational movement to a linear movement using a ball screw or another screw shaft.

What is claimed is:

1. A motion control system for moving a moving body by a desired amount of movement, the motion control system comprising:
    moving-body-driving means for moving the moving body;
    a scale provided on the moving body or on an object that moves integrally with the moving body;
    a plurality of scale-detecting means for detecting the scale and outputting a periodic wave signal;
    computation means for calculating an average value of the amount of movement based on values obtained by performing interpolation on each of the output signals as periodic wave signals from the scale-detecting means, and outputting the average value of the amount of movement as a calibrated angle data signal; and
    control means for controlling the moving-body-driving means based on the calibrated angle data signal.

2. The motion control system according to claim 1, wherein the time between the computation means receiving the output from the scale-detecting means and the computation means outputting the calibrated angle data signal is 20 µs or less.

3. The motion control system according to claim 1, wherein
    the moving body is a rotating body;
    the scale is provided directly around the moving body or provided on an object that moves integrally with the moving body; and
    the scale-detecting means are provided around the rotating body at regular intervals.

4. The motion control system according to claim 1, wherein
    the scale-detecting means include, as a single group, n reading heads arranged at regular intervals (where n is 2, 3, 5, or another prime number);
    have a data storage table in which error components of a higher order than an nth-order error component of the group are stored; and
    combine angle data obtained by the computation means with an error component stored in the data storage table.

5. The motion control system according to claim 4, wherein the scale-detecting means are configured so as to include a plurality of groups of reading heads of different values of n.

6. The motion control system according to claim 5, wherein each of the groups of the scale-detecting means has at least one reading head that also belongs to another group.

7. The motion control system according to claim 1, wherein the scale-detecting means output a periodic wave signal which is an AB signal that includes an A-phase and a B-phase which are waves having different phases from each other.

8. The motion control system according to claim 1, wherein the scale-detecting means output a periodic wave signal which is an AB signal that includes an A-phase, which is a cosine wave; and a B-phase, which is a sine wave; or an ABZ signal that includes, in addition to the A-phrase and the B-phrase, a Z-signal that represents a reference position.

9. An X-ray measurement apparatus having a goniometer for causing an X-ray source and an X-ray detector to rotate by a predetermined angle; wherein
    the goniometer has a first motion control system configured from the motion control system according to claim 1, and a second motion control system configured from the motion control system according to claim 1;
    the moving body included in the first motion control system and the second motion control system is a rotary stage that rotates about an axis passing through the rotary stage;
    the X-ray source is supported by the rotary stage included in the first motion control system; and
    the X-ray detector is supported by the rotary stage included in the second motion control system.

* * * * *